(12) United States Patent
Shi et al.

(10) Patent No.: US 9,029,344 B2
(45) Date of Patent: May 12, 2015

(54) LINKED PURINE PTERIN HPPK INHIBITORS USEFUL AS ANTIBACTERIAL AGENTS

(75) Inventors: Genbin Shi, Frederick, MD (US); Gary X. Shaw, North Potomac, MD (US); Xinhua Ji, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 45 days.

(21) Appl. No.: 13/704,857

(22) PCT Filed: Jun. 1, 2011

(86) PCT No.: PCT/US2011/038744
§ 371 (c)(1),
(2), (4) Date: Dec. 17, 2012

(87) PCT Pub. No.: WO2011/159471
PCT Pub. Date: Dec. 22, 2011

(65) Prior Publication Data
US 2013/0172285 A1    Jul. 4, 2013

Related U.S. Application Data

(60) Provisional application No. 61/356,213, filed on Jun. 18, 2010.

(51) Int. Cl.
| | | |
|---|---|---|
| *A61K 31/70* | (2006.01) | |
| *A61K 31/50* | (2006.01) | |
| *C07H 19/16* | (2006.01) | |
| *C07D 475/00* | (2006.01) | |
| *C07H 19/167* | (2006.01) | |
| *C07D 475/04* | (2006.01) | |
| *G06F 19/16* | (2011.01) | |

(52) U.S. Cl.
CPC ............ *C07H 19/167* (2013.01); *C07D 475/04* (2013.01); *G06F 19/16* (2013.01)

(58) Field of Classification Search
None
See application file for complete search history.

(56) References Cited

U.S. PATENT DOCUMENTS 4,036,961 A    7/1977 Stuart

FOREIGN PATENT DOCUMENTS

EP    0884317 B1    5/2005

OTHER PUBLICATIONS

Al-Hassan et al., "Specific Inhibitors in Vitamin Biosynthesis. Part 7. Syntheses of Blocked 7,8-Dihydropteridines via a-Amino Ketones", Journal of the Chemical Society, Perkin Transactions 1, Jan. 1, 1985, pp. 1645-1659.

Brown et al., "Synthesis and Reactions of 7,8-Diydro-8-methylpterin and 9-Methyl-guanine 7-Oxide", Journal of the Chemcial Society, Perkin Transactions 1, No. 9, Jan. 1, 1977, pp. 1003-1009.
Extended European Search Report for European Application No. 11796158.1, Application Filing Date Jun. 1, 2011, Date of Completion of the Search Report Oct. 24, 2013, 11 pages.
Mengel et al., "Pteridine, LXVI: Synthese und Eigenschaften von Dihydro- und Tetrahydro- Derivaten der Pterin-6,7-dicarbonsaure*)", with English Abstract, Chemische Bericht, vol. 111, No. 12, Dec. 1, 1978, pp. 3790-3805.
Wang et al., "A Point Mutation Converts Dihydroneopterin Aldolase to a Cofactor-Independent Oxygenases", Journal of the American Chemical Society, vol. 128, No. 40, Oct. 1, 2006, pp. 13216-13223.
Blaszczyk et al. "Reaction Trajectory of Pyrophosphoryl Transfer Catalyzed by 6-Hydroxymethyl-7,8-Dihydropterin Pyrophosphokinase" Structure, vol. 12, 2004, pp. 467-475.
Blaszczyk et al. "Catalytic Center Assembly of HPPK as Revealed by the Crystal Structure of a Ternary Complex at 1.25 Å Resolution" Structure, vol. 8, Oct. 2000, pp. 1049-1058.
Hennig et al. "The Structure and Function of the 6-Hydroxymethyl-7,8-dihydropterin Pyrophosphokinase From *Haemophilus influenzae*" Journal of Molecular Biology, 1999, 287, pp. 211-219.
Japanese Patent Publication No. 06-056669: Publication Date: Mar. 1, 1994; 1 Page, English Abstract Only.
Written Opinion of the International Searching Authority for International Application No. PCT/US2011/038744, International Filing Date: Jun. 1, 2011; Date of Mailing: Feb. 17, 2012, 6 Pages.
International Search Report of the International International Searching Authority for International Application No. PCT/US2011/038744; International Filing Date: Jun. 1, 2012; Date of Mailing: Feb. 17, 2012; 6 Pages.

(Continued)

*Primary Examiner* — Traviss C McIntosh, III
(74) *Attorney, Agent, or Firm* — Cantor Colburn LLP

(57) ABSTRACT

The disclosure provides linked purine pterin compounds and analogs thereof that are novel HPPK inhibitors. The HPPK inhibitors described herein are compounds and the pharmaceutically acceptable salts thereof of general Formula I (Formula I)

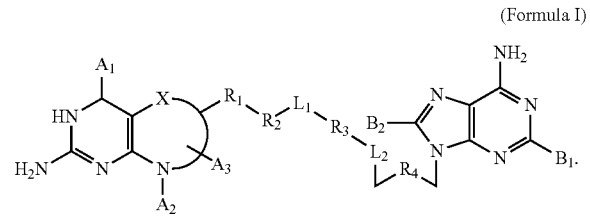

The variables, e.g. $A_1$ to $A_3$, $R_1$ to $R_4$, $L_1$, $L_2$, $B_1$, and $B_2$ are described herein. Compounds and salts of Formula I bind to HPPK with high affinity and specificity. Pharmaceutical compositions containing an HPPK inhibitor of Formula I and methods of treating a bacterial infection in a patient by providing one or more HPPK inhibitors of Formula I to the patient are also provided. Processes and intermediates useful for preparing compounds of Formula I are also provided. Methods of using the disclosed compounds to guide the development of additional novel anti-bacterial agents are also provided.

14 Claims, 4 Drawing Sheets

(56) References Cited

OTHER PUBLICATIONS

Shi et al. "Bisubstrate Analogue Inhibitors of 6-Hydroxymethyl-7,8-dihydropterin Pyrophosphokinase: Synthesis and Biochemical and Crystallographic Studies" Journal of Medical Chemistry, vol. 44, 2000, pp. 1364-1371.

Shi et al. "New Ways to Derivatize at Position 6 of 7,7-dimethyl-7,8-dihydropterin" Tetrahedron Letters, 52, 2011, pp. 6174-6176.

Wood, "Specific Inhibition of Dihydrofolate Biosynthesis—A New Approach to Chemotherapy" Chemistry and Biology of Pteridines, 1975, pp. 27-49.

HPPK catalyzes the transfer of pyrophosphate from ATP to 6-hydroxymethyl-7,8-dihydropterin (HP)

SEQUENCE LISTING

<160> NUMBER OF SEQ ID NOS: 1

<210> SEQ ID NO 1
<211> LENGTH: 159
<212> TYPE: PRT
<213> ORGANISM: Staphylococcus aureus

<400> SEQUENCE: 1

```
Met Thr Val Ala Tyr Ile Ala Ile Gly Ser Asn Leu Ala Ser Pro Leu
1               5                   10                  15

Glu Gln Val Asn Ala Ala Leu Lys Ala Leu Gly Asp Ile Pro Glu Ser
            20                  25                  30

His Ile Leu Thr Val Ser Ser Phe Tyr Arg Thr Pro Pro Leu Gly Pro
        35                  40                  45

Gln Asp Gln Pro Asp Tyr Leu Asn Ala Ala Val Ala Leu Glu Thr Ser
    50                  55                  60

Leu Ala Pro Glu Glu Leu Leu Asn His Thr Gln Arg Ile Glu Leu Gln
65                  70                  75                  80

Gln Gly Arg Val Arg Lys Ala Glu Arg Trp Gly Pro Arg Thr Leu Asp
                85                  90                  95

Leu Asp Ile Met Leu Phe Gly Asn Glu Val Ile Asn Thr Glu Arg Leu
                100                 105                 110

Thr Val Pro His Tyr Asp Met Lys Asn Arg Gly Phe Met Leu Trp Pro
            115                 120                 125

Leu Phe Glu Ile Ala Pro Glu Leu Val Phe Pro Asp Gly Glu Met Leu
        130                 135                 140

Arg Gln Ile Leu His Thr Arg Ala Phe Asp Lys Leu Asn Lys Trp
145                 150                 155
```

LINKED PURINE PTERIN HPPK INHIBITORS USEFUL AS ANTIBACTERIAL AGENTS

CROSS REFERENCE TO RELATED APPLICATION

This application is a national stage application of PCT/US2011/038744, filed Jun. 1, 2011, which claims priority from U.S. Provisional Appl. No. 61/356,213, filed Jun. 18, 2010, both of which are hereby incorporated by reference in their entirety.

FIELD OF THE DISCLOSURE

The disclosure provides linked purine pterin compounds that are novel HPPK inhibitors and new intermediates for the synthesis of such compounds. These linked purine pterin inhibitors bind to HPPK with high affinity and specificity. Pharmaceutical compositions containing HPPK inhibitors and methods of treating a bacterial infection in a patient with one or more of the HPPK inhibitors of the disclosure are also provided. Methods of using the disclosed compounds and intermediates to guide the development of additional novel anti-bacterial agents are also provided.

BACKGROUND

Folate cofactors are essential for life. Mammals derive folates from their diet, whereas most microorganisms must synthesize folates de novo. Therefore, the folate pathway is an ideal target for developing anti-bacterial agents. For example, inhibitors of two enzymes in the pathway, dihydropteroate synthase and dihydrofolate reductase, are currently used as antibiotics. 6-Hydroxymethyl-7,8-dihydropterin pyrophosphokinase (E.C. 2.7.6.3, HPPK), a kinase responsible for an essential step in the biosynthesis of folic acid, catalyzes the transfer of pyrophosphate from ATP to 6-hydroxymethyl-7,8-dihydropterin (HP) (FIG. 1) (Shiota, T., 1984, in *Chemistry and Biochemistry of Folates*, R. T. Blakley, and S. J. Benkovic, eds. pp. 121-134, New York: John Wiley & Sons). No existing antibiotic is known to modulate HPPK activity. Due to in-depth structural and mechanistic studies of HPPK, this enzyme is well understood and therefore a good target for novel anti-bacterial compounds.

Two types of HPPK inhibitors (FIG. 1) have been reported (Derrick, J. P. (2008) The structure and mechanism of 6-hydroxymethyl-7,8-dihydropterin pyrophosphokinase, in G. Litwack, ed. *Folic Acid and Folates*, (Oxford, UK: Academic Press). Type 1 inhibitors are HP derivatives, including HP-1 (Hennig, M. et al., J. Mol. Biol. (1999) 287: 211-219; Wood, H. C. S. (1975) Specific inhibition of dihydrofolate biosynthesis—A new approach to chemotherapy, in *Chemistry and Biology of Pteridines*, W. Pfleiderer, ed. (Berlin-New York: Walter de Gruyter)) and HP-3. Type 2 inhibitors are bisubstrate analogues HP$_n$A (n=2, 3, or 4) (Shi, G. et al., J. of Med. Chem. (2001) 44: 1364-1371). No pharmaceutically useful HPPK inhibitors have been identified to date. Thus, there remains a need for novel and useful HPPK inhibitor antibacterial compounds. The present disclosure fulfills this need and provides further advantages, which are set forth below.

SUMMARY

Compound of Formula I

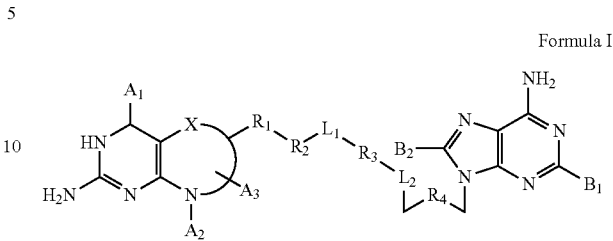

Formula I and the pharmaceutically acceptable salts thereof are provided herein. Within Formula I the variables, e.g. $A_1$ to $A_3$, $R_1$ to $R_4$, $L_1$, $L_2$, $B_1$, and $B_2$ carry the following definitions.

The cyclic group is a 5- or 6-membered heterocyclic ring in which X is nitrogen, —N($A_5$)-, —C($A_6$)-, or —C($A_6A_7$)-.

$A_1$ is hydrogen, oxo, amino, or amino$C_1$-$C_2$alkyl.

$A_2$ is absent, hydrogen, or $C_1$-$C_2$alkyl.

$A_3$ is absent, or one or two substituents independently chosen from hydrogen, halogen, $C_1$-$C_2$alkyl, and $C_1$-$C_2$alkoxy.

$A_5$ is hydrogen or $C_1$-$C_4$alkyl.

$A_6$ and $A_7$ are independently hydrogen, $C_1$-$C_4$alkyl, or $C_1$-$C_4$alkoxy.

$R_1$ is methylene, optionally substituted with hydroxyl, halogen, $C_1$-$C_2$alkyl, or $R_2$ is chosen from —NH—, —SH—, —S(=O)—, —S(=O)$_2$—, —P(=O)—, and —P(=O)$_2$—.

$L_1$ is an alkylene linker having from 1 to 4 carbon atoms, optionally containing 1 heteroatom selected from oxygen, nitrogen, and sulfur, and optionally containing 1 to 2 carbon-carbon double bonds, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy.

$R_3$ is absent or $R_3$ is an amide, heteroalkylene, cycloalkyl, heterocycloalkyl, phenyl, or 5- or 6-membered heteroaryl; and $R_3$ is unsubstituted or substituted with 1 or more substituents independently chosen from hydroxyl, halogen, amino, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

$L_2$ is absent or $L_2$ is an alkylene linker having from 1 to 4 carbon atoms, optionally containing 1 heteroatom selected from oxygen, nitrogen, sulfur, and phosphorus and optionally containing 1 to 2 carbon-carbon double bonds, wherein $L_2$ is unsubstituted or substituted with 1 or more substituents independently chosen from oxo, hydroxyl, halogen, amino, $C_1$-$C_4$alkyl, $C_1$-$C_4$alkoxy, $C_1$-$C_2$haloalkyl, and $C_1$-$C_2$haloalkoxy.

$R_4$ is a 5- or 6-membered monosaccharide ring or $R_1$ is an alkylene or heteroalkylene linker having from 1 to 4 chain atoms.

B$_1$ and B$_2$ are independently chosen from hydrogen, halogen, hydroxyl, amino, C$_1$-C$_2$alkyl, C$_1$-C$_2$alkoxy, mono- or di-C$_1$-C$_2$alkylamino, aminoC$_1$-C$_2$alkyl, C$_1$-C$_2$haloalkyl, and C$_1$-C$_2$haloalkoxy.

Pharmaceutical compositions comprising a compound or salt of Formula I together with a pharmaceutically acceptable carrier are further provided herein.

A method of treating a condition responsive to HPPK modulation, comprising providing a therapeutically effective amount of compound to a patient having a condition response to HPPK modulation is also provided herein. Conditions responsive to HPPK modulation include bacterial infections.

DETAILED DISCLOSURE

Terminology

Figure 1:
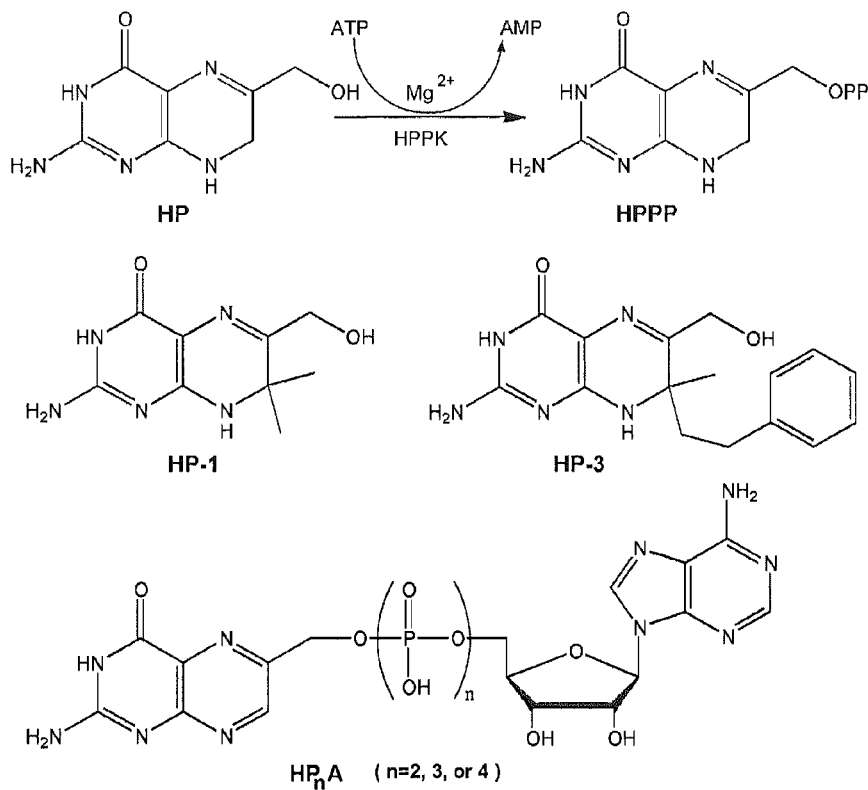
FIG. 1. Scheme showing HPPK catalyzing the transfer of pyrophosphate from ATP to 6-hydroxymethyl-7,8-dihydropterin.

It is helpful to provide definitions of certain terms to be used herein, prior to setting out the disclosure in detail.

Presently disclosed compounds are described using standard nomenclature. Unless defined otherwise, all technical and scientific terms used herein have the same meaning as is commonly understood by one of skill in the art to which this disclosure belongs. Unless clearly contraindicated by the context each compound name includes the free acid or free base form of the compound as all pharmaceutically acceptable salts of the compound.

The phrase "compounds of Formula I" encompasses all compounds that satisfy Formula I, including any enantiomers, racemates and stereoisomers, as well as all pharmaceutically acceptable salts of such compounds and also includes all subgeneric groups of Formula I, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate and does not pose a limitation on the scope of the disclosure unless otherwise claimed. No language in the specification should be construed as indicating any non-claimed element as essential to the practice as used herein. Unless defined otherwise, technical and scientific terms used herein have the same meaning as is commonly understood by one of skill in the art to which this disclosure belongs.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C═O)NH$_2$ is attached through carbon of the keto (C═O) group.

A bond represented by a combination of a solid and dashed line, i.e., ═══, may be either a single or double bond.

"Alkyl" is a branched or straight chain saturated aliphatic hydrocarbon group, having the specified number of carbon atoms, generally from 1 to about 12 carbon atoms. The term C$_1$-C$_6$alkyl indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. C$_1$-C$_8$alkyl, C$_1$-C$_4$alkyl, and C$_1$-C$_2$alkyl. When C$_0$-C$_n$ alkyl is used herein in conjunction with another group, for example, (aryl)C$_0$-C$_4$ alkyl, the indicated group, in this case aryl, is either directly bound by a single covalent bond (C$_0$), or attached by an alkyl chain having the specified number of carbon atoms, in this case 1, 2, 3, or 4 carbon atoms. C$_0$-C$_n$alkyl is used in conjunction with heteroaryl, aryl, phenyl, cycloalkyl, and heterocycloalkyl, e.g., (5- to 10-membered heteroaryl)C$_0$-C$_2$alkyl, (aryl)C$_0$-C$_2$alkyl, (phenyl)C$_0$-C$_2$alkyl, (C$_3$-C$_7$cycloalkyl)C$_0$-C$_4$alkyl, and (heterocycloalkyl)C$_0$-C$_4$alkyl. Examples of alkyl include, but are not limited to, methyl, ethyl, n-propyl, isopropyl, n-butyl, 3-methylbutyl, t-butyl, n-pentyl, and sec-pentyl.

"Alkylene" is a saturated organic radical of the formula —(CH$_2$)$_n$— where n is the number of CH$_2$ groups in the alkylene radical. Alkylene radicals having from 1 to 6 carbons or from 1 to 4 carbons are usually preferred. Likewise "heteroalkylene" is a saturated organic radical of the formula —(CH$_2$)$_n$— where n is the number of CH$_2$ groups in the chain and the alkylene chain is interrupted at one or more points, usually one point, with a covalently bound heteroatom selected from nitrogen, oxygen, sulfur, and phosphorous.

"Alkoxy" is an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Aryl" is an aromatic group containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl. An "aryloxy"

group is an aryl group as described herein bound to the group it substitutes via an oxygen bridge.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane.

"Haloalkyl" is both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, furanyl, imidazolyl, indolyl, and isoxazolyl.

"Heterocycloalkyl" is a saturated monocyclic group having the indicated number of ring atoms and containing from 1 to about 3 heteroatoms chosen from N, O, and S, with remaining ring atoms being carbon, or a saturated bicyclic ring system having at least one N, O, or S ring atom with the remaining atoms being carbon. Monocyclic heterocycloalkyl groups usually have from 4 to about 8 ring atoms. In some embodiments monocyclic heterocycloalkyl groups have from 5 to 7 ring atoms.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

A "monosaccharide" is any of several carbohydrates, such as tetroses, pentoses, and hexoses, which cannot be broken down to simpler sugars by hydrolysis. When a monosaccharide is recited as a component of Formula I a divalent radical of a monosaccharide is intended. Such a monosaccharide is covalently bound through the oxygen atoms of two of its hydroxyl groups to the purine nitrogen and $L_2$ (if present) or $R_3$ (if $L_2$ is absent) or $L_1$ (if both $L_2$ and $R_3$ are absent).

The term "substituted" means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$–$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g., coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier.

Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like.

The term "carrier" applied to pharmaceutical compositions of the disclosure refers to a diluent, excipient, or vehicle with which an active compound is provided. An excipient is an inactive ingredient useful in preparing a pharmaceutical composition that is generally safe, non-toxic, and neither biologically nor otherwise undesirable, and includes an excipient that is acceptable for veterinary use as well as human pharmaceutical use.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment" as used herein includes providing a compound of Formula I, either as the only active agent or together with at least one additional active agent sufficient to: (a) inhibiting the disease, i.e., arresting its development; and (b) relieving the disease, i.e., causing regression of the disease. Bacterial infections, such as bacterial infections and fungal infections, are included in the diseases treated with a compound of Formula I. "Treating" and "treatment" also means providing a therapeutically effective amount of a compound of Formula I, as the only active agent or together with at least one additional active agent to a patient having a bacterial infection.

A "therapeutically effective amount" of a compound of Formula I or composition of this disclosure means an amount effective, when administered to a patient, to provide a therapeutic benefit such as an amelioration of symptoms, e.g., an amount effective to decrease the symptoms of a bacterial infection. For example a patient having a bacterial infection may present elevated levels of certain liver enzymes or an elevated white blood cell count. A therapeutically effect amount is thus an amount sufficient to provide a significant reduction in elevated liver enzyme levels or white blood cell count, or an amount sufficient to provide a return of the liver enzyme levels or white blood cell count to the normal range. A therapeutically effective amount is also an amount sufficient to prevent a significant increase or significantly reduce the detectable level of bacterial particles or anti-bacterial antibodies in the patient's blood, serum, or tissues.

A "significant reduction" in the detectable level of bacterial particles or anti-bacterial antibodies is any detectable reduction that is statistically significant in a standard parametric test of statistical significance such as Student's T-test, where $p<0.05$.

Chemical Description

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present disclosure. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral high pressure liquid chromatography (HPLC) column.

Where a compound exists in various tautomeric forms, the disclosure is not limited to any one of the specific tautomers, but rather includes all tautomeric forms.

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g., $A_1$ to $A_3$, $R_1$ to $R_4$, $L_1$, $L_2$, $B_1$, and $B_2$. Unless otherwise specified, each variable within such a formula is defined independently of other variables. Thus, if a group is said to be substituted, e.g., with 0-2 R*, then the group may be substituted with up to two R* groups and R* at each occurrence is selected independently from the definition of R*. Also, combinations of substituents and/or variables are permissible only if such combinations result in stable compounds.

In addition to compounds of Formula I as described above, the disclosure also includes compounds of Formula I in which one or more of the following conditions is met for the variables in Formula I. Compounds having any combination of the variable definitions set forth below that result in a stable compound are included in the disclosure.

Thus in addition to compounds of Formula I, the disclosure provides compounds and salts thereof of Formula II.

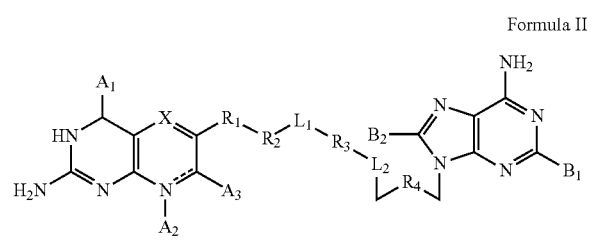

Formula II

Within Formula II the following conditions are met.
$A_2$ is absent or hydrogen.
$A_3$ is one or two substituents independently chosen from hydrogen and $C_1$-$C_2$alkyl; and
X is N or —C($A_6$)-.
The remaining variables carry the definitions set forth for Formula I.

Also provided herein are compounds and salts thereof of Formula III and IV.

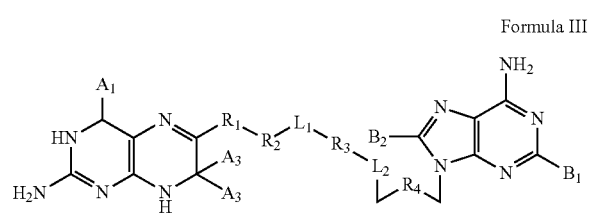

Formula III

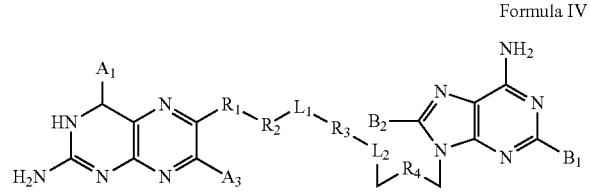

Formula IV

Within Formula III and IV the following conditions are met.
$A_3$ are each independently hydrogen, halogen, methyl, or methoxy.
$R_3$ is a 5- or 6-membered heterocycloalkyl group having 1 or 2 nitrogen ring atoms with remaining ring atoms being carbon, and $R_3$ is unsubstituted or substituted with 1 or more substituents independently chosen from hydroxyl, halogen, amino, $C_1$-$C_2$alkyl, and $C_1$-$C_2$alkoxy.
$R_4$ is a 5- or 6-membered monosaccharide ring.

The remaining variables carry the definitions set forth for Formula I.

The disclosure also provides compounds and salts thereof of Formula I in which one or more of the following conditions are met.
$A_3$ is hydrogen, halogen, methyl, or methoxy,
$R_3$ is a 5- or 6-membered heterocycloalkyl group having 1 or 2 nitrogen ring atoms with remaining ring atoms being carbon, wherein $R_3$ is unsubstituted or substituted with 1 or more substituents independently chosen from hydroxyl, halogen, amino, and $C_1$-$C_2$alkyl, $C_1$-$C_2$alkoxy; and
$R_4$ is a 5 or 6-membered monosaccharide ring.
$A_1$ is oxo and each $A_3$ is independently chosen from hydrogen and methyl.
$R_1$ is methylene optionally substituted with —(C=O)—.
$R_2$ is —NH—.
$L_1$ is an alkylene linker having from 2 to 4 carbon atoms, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy; and
$L_2$ is an alkylene linker having from 1 to 2 carbon atoms, containing 1 heteroatom selected from oxygen, nitrogen, and sulfur, wherein $L_2$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy.

The total number of carbon atoms in the $L_1$ and $L_2$ alkylene linkers is from 3 to 5.
$L_1$ is an alkylene linker having from 2 to 3 carbon atoms, wherein $L_1$ is unsubstituted or substituted with 1 or more substituents independently chosen from halogen and methyl; and
$L_2$ is an alkylene linker of the formula —$SCH_2$—, wherein $L_2$ is unsubstituted or substituted with one or more substituents independently chosen from halogen and methyl.
$R_3$ is a piperidinyl, piperazinyl, or pyrrolidinyl ring; each of which $R_3$ is unsubstituted or substituted with 1 or more substituents independently chosen from hydroxyl, halogen, $C_1$-$C_2$alkyl, and $C_1$-$C_2$alkoxy.
$R_4$ is a 5- or 6-membered monosaccharide ring.
$R_4$ is d-ribose, d-arabinose, d-xylose, or d-lyxose.
$R_4$ is d-ribose and $B_1$ and $B_2$ are both hydrogen.
Also provided are compounds and salts thereof of Formula V

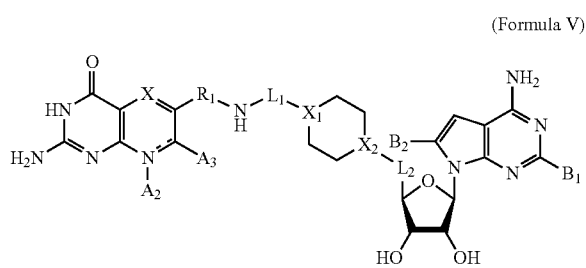

(Formula V)

Within Formula V the following conditions are met.
$A_1$ is oxo.
$A_2$ is absent or hydrogen.
$A_3$ is one or two substituents independently chosen from hydrogen and $C_1$-$C_2$ alkyl.
X is N or —C($A_6$)-.
$X_1$ and $X_2$ are independently CH or N.
$R_1$ is methylene optionally substituted with —(C=O)—.

$L_1$ is an alkylene linker having from 2 to 4 carbon atoms, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy.

$L_2$ is an alkylene linker having from 1 to 2 carbon atoms, containing 1 heteroatom selected from oxygen, nitrogen, and sulfur, wherein $L_2$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy.

$B_1$ and $B_2$ are independently hydrogen or methyl.

Synthetic Methods and Intermediates

This disclosure includes synthetic methods for producing compounds of Formula I. The disclosure also includes synthetic intermediates useful for producing compounds of Formula I. Particularly this disclosure includes compounds of Formula A

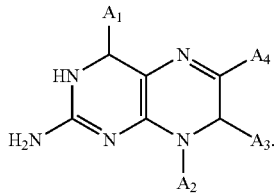

(Formula A)

Within Formula A, $A_1$ is hydrogen, oxo, amino, or amino ($C_1$-$C_2$alkyl); $A_2$ is hydrogen or $C_1$-$C_2$alkyl; $A_3$ is one or two substituents independently chosen from hydrogen and $C_1$-$C_2$alkyl; and $A_4$ is a formyl group or $C_1$-$C_4$alkylester. The disclosure includes intermediate compounds 25 and 26.

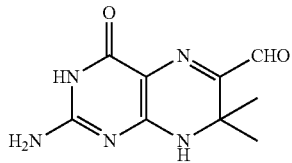

(Compound 25)

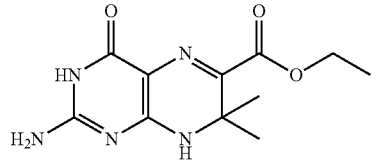

(Compound 26)

Synthetic methods for preparing intermediate compounds of Formula A, including compounds 25 and 26 are provided in Scheme 3. Compound 25 is prepared by methyl group direct oxidation of the 6-methyl pterin with $SeO_2$, for which experimental details are provided in Example 2. Compound 26 is prepared by bromination of the 6-methyl pterin followed by hydrolysis to the 6-carboxylic acid ethyl ester, for which experimental details are provided in Example 3.

Pharmaceutical Preparations

Compounds disclosed herein can be administered as the neat chemical, but are preferably administered as a pharmaceutical composition. Accordingly, pharmaceutical compositions comprising a compound or pharmaceutically acceptable salt of Formula I, together with at least one pharmaceutically acceptable carrier are provided herein. The pharmaceutical composition may contain a compound or salt of Formula I as the only active agent, or may contain one or more additional active agents.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compounds described herein.

The pharmaceutical compositions can be formulated for oral administration. These compositions contain between 0.1 and 99 weight % (wt. %) of a hydrazone or a diacyl hydrazine compound and usually at least about 5 wt. % of a hydrazone or a diacyl hydrazine compound. Some embodiments contain from about 25 wt. % to about 50 wt. % or from about 5 wt. % to about 75 wt. % of the hydrazone or diacyl hydrazine compound.

Methods of Treatment

Methods of treating bacterial infections by providing an effective amount of a compound of the invention to a patient having a bacterial infection are provided. A compound as described herein may be provided as the only active agent or may be provided together with one or more additional active agents. Bacterial infections that may be treated with compounds of Formula I include, but are not limited to, *Escherichia coli, Yersinia pestis, Bacillus anthracis, Francisella tularensis, Staphylococcus aureus, Enterococcus faecalis, Mycobacterium tuberculosis*, and *Helicobacter pylori* infections.

The pharmaceutical combinations disclosed herein are useful for treating bacterial infections in human and non-human patients. Non-human patients include, for example, livestock animals and companion animals.

An effective amount of a pharmaceutical combination as provided by this disclosure may be an amount sufficient to (a) cause a regression of the bacterial infection; or (b) cause a cure of a bacterial infection such that bacterial particles, or anti-bacterial antibodies, can no longer be detected in a previously infected patient's blood or plasma. An amount of a pharmaceutical composition needed to inhibit the progress or cause a regression of a bacterial infection, includes an amount effective to stop the worsening of symptoms of the infection or reduce the symptoms experienced by an infected patient. Alternatively a halt in progression or regression of infections may be indicated by any of several markers for the disease. For example, a lack of increase or reduction in the number of bacterial particles in the patient's blood or serum, or a lack of increase or reduction in the number of circulating anti-bacterial antibodies in a patient's blood, or return to normal for the patient's white blood cell count are markers of a halt in progression or regression of bacterial infection.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

Methods of treatment include providing certain dosage amounts of a compound of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage unit a compound of Formula I. In certain embodiments 25 mg to 500 mg, or 25 mg to 200 mg of a compound of Formula I are provided daily to a patient. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

Methods comprising providing a compound or salt of Formula I in a container together with instructions for using the composition to treat a patient suffering from a bacterial infection are included herein.

Packaged pharmaceutical combinations are also included herein. Such packaged combinations include a compound of Formula I in a container together with instructions for using the combination to treat or prevent a viral infection, such as a bacterial infection, in a patient.

The packaged pharmaceutical combination may include one or more additional active agents.

Combination Methods

Pharmaceutical compositions and methods of treatment in which a compound or salt of Formula I is provided together with one or more additional active agents are included herein. In certain embodiments the active agent (or agents) is an anti-bacterial compound such as an antibiotic. The compound of Formula I and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods disclosed herein comprise administering or delivering the compound of Formula I and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Crystal Structures of Compound 13, 24, or 28 in Complex with HPPK.

HPPK in complex with 13, 24, or 28 (HPPK•BSS10113, HPPK•BSS10124, or HPPK•BSS10128) was crystallized (Table 1).

TABLE 1

| Crystallization Conditions | HPPK•BSS10113 | HPPK•BSS10124 | HPPK•BSS10128 |
|---|---|---|---|
| Protein Solution | | | |
| HPPK (mg/mL) | 10 | 10 | 10 |
| BSS10113 | saturated | | |
| BSS10124 | | Saturated | |
| BSS10128 | | | Saturated |
| Tris-HCl [mM (pH)] | 20 (8.0) | 20 (8.0) | 20 (8.0) |
| Reservoir Solution | | | |
| PEG 3350 [% (w/v)] | 25 | 25 | 20 |
| $CH_3COONH_4$ (mM) | | 200 | 200 |
| Bis-Tris [mM (pH)] | 100 (6.5) | 100 (8.5) | |
| HEPES [mM (pH)] | | | 100 (7.5) |
| Crystals | | | |
| Appear (days) | 7 | 7 | 14 |
| Final size (days) | 14 | 14 | 21 |
| Shape | Thin plate | Thin plate | Thin plate |
| Dimension (mm) | 0.15 × 0.10 × 0.005 | 0.10 × 0.05 × 0.005 | 0.15 × 0.10 × 0.005 |

The structures of the three complexes were determined (Table 2).

TABLE 2

Crystals, X-ray Diffraction Data, and Structures

| | HPPK•BSS10113 | HPPK•BSS10124 | HPPK•BSS10128 |
|---|---|---|---|
| Crystal | | | |
| Space group | C2 | P2$_1$2$_1$2 | P2$_1$2$_1$2 |
| Unit cell parameters: a (Å) | 79.98 | 52.91 | 53.00 |
| b (Å) | 52.77 | 70.98 | 70.64 |
| c (Å) | 36.69 | 36.38 | 36.25 |
| β (°) | 102.70 | 90 | 90 |
| Matthews coefficient (Å$^3$/Da) | 2.1 | 1.9 | 1.9 |
| Data Statistics | Overall (last shell) | Overall (last shell) | Overall (last shell) |
| Resolution (Å) | 30-2.00 (2.07-2.00) | 30-1.89 (1.96-1.89) | 30-1.88 (1.95-1.88) |
| Unique reflections | 9255 (695) | 10823 (808) | 10756 (794) |
| Redundancy | 6.6 (5.9) | 6.4 (3.5) | 6.3 (4.0) |
| Completeness (%) | 90.8 (70.1) | 93.9 (72.1) | 92.9 (69.8) |
| R$_{merge}$[a] | 0.081 (0.238) | 0.082 (0.472) | 0.074 (0.325) |
| I/σ | 20.8 (5.5) | 19.3 (2.1) | 20.2 (3.1) |
| Structure Solution | | | |
| Method | Fourier synthesis | Fourier synthesis | Fourier synthesis |
| Model | PDB 1EQM | PDB entry 3ILJ | HPPK·BSS10124 |
| Refinement Statistics | Overall (last shell) | Overall (last shell) | Overall (last shell) |
| Resolution (Å) | 30-2.00 (2.13-2.00) | 30-1.89 (1.99-1.89) | 30-1.88 (1.98-1.88) |
| Unique reflections | 9247 (1202) | 10792 (1178) | 10753 (1052) |
| Completeness (%) | 90.7 (72.0) | 93.9 (74.0) | 92.8 (72.0) |
| Data in the test set | 824 (107) | 1000 (109) | 919 (98) |
| R-work | 0.158 (0.168) | 0.216 (0.271) | 0.205 (0.242) |
| R-free | 0.208 (0.260) | 0.276 (0.328) | 0.270 (0.278) |
| Structure Statistics | | | |
| Protein non-H atoms/B (Å$^2$) | 1448/34.7 | 1422/31.0 | 1388/25.6 |
| Heterogen atoms/B (Å$^2$) | 45/49.1 | 47/4.1 | 48/40.8 |
| Water oxygen atoms/B (Å$^2$) | 107/43.1 | 107/39.3 | 94/30.9 |
| Rmsd | | | |
| Bond lengths (Å) | 0.008 | 0.005 | 0.008 |
| Bond angles (°) | 0.957 | 0.778 | 0.972 |
| Coordinate error (Å) | 0.29 | 0.14 | 0.29 |
| Ramachandran plot[b] | | | |
| Favored regions (%) | 98.7 | 97.3 | 97.3 |
| Disallowed regions (%) | 0.0 | 0.0 | 0.0 |

[a] $R_{merge} = \Sigma|(I-\langle I \rangle)|/\Sigma(I)$, where I is the observed intensity.
[b] Obtained using Ramachandran data (Lovell et al., Proteins (2003) 50: 437-450).

Figure 3:
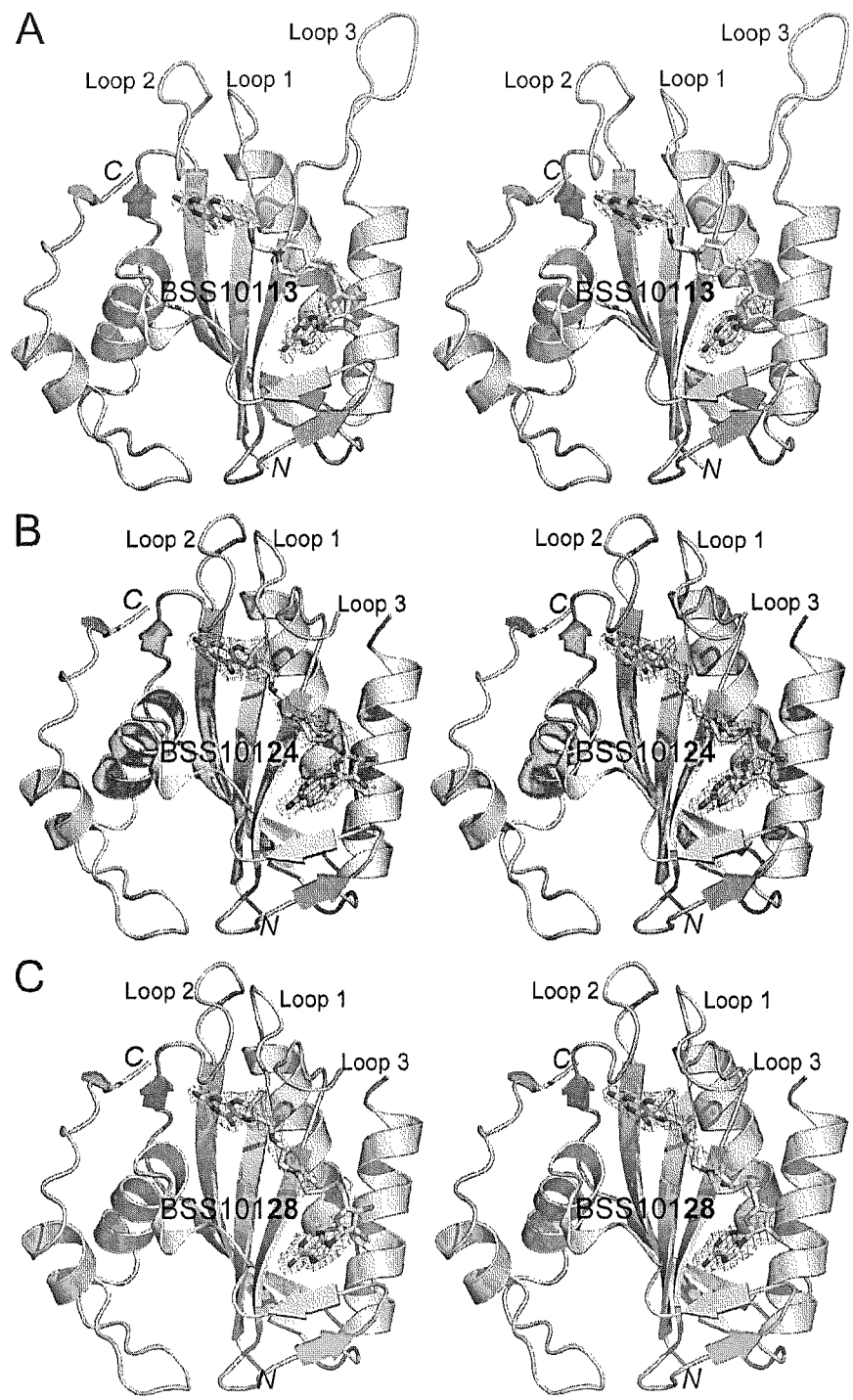
FIG. 3. Stereo illustration of the (A) HPPK•BSS10113, (B) HPPK•BSS10124, and (C) HPPK•BSS10128 structure. Polypeptide chains are shown as a ribbon diagrams. Ligands are shown as sticks and overlapped with the 2F$_o$-F$_c$ annealed omit maps contoured at 0.9 σ (nets in blue).

The 2.0-Å structure of HPPK•BSS10113 contains 1 HPPK, 1 BSS10113, 1 ethylene glycol molecule, and 107 water molecules (FIG. 3A), in which the overall conformation of HPPK is similar to that observed in the HPPK•MgADP complex (PDB entry 1EQM), in which Loop 3 moves dramatically away from the active center.

The 1.89-Å structure of HPPK•BSS10124 contains 1 HPPK, 1 BSS10124, 1 acetate ion, and 89 water molecules (FIG. 3B), in which the overall conformation of HPPK is similar to that observed in the HPPK-HP-MgAMPCPP complex (PDB entry 1Q0N). However, part of Loop 3 in the HPPK•BSS10124 structure is disordered; no electron density was observed for residues 83-86.

The 1.88-Å structure of HPPK•BSS10128 contains 1 HPPK, 1 BSS10128, 1 acetate ion, and 94 water molecules (FIG. 3C), in which the overall conformation of HPPK is similar to the HPPK•BSS10124 complex with disordered residues 83-86.

The disclosure includes crystals of HPPK and inhibitors. For example the disclosure includes the following HPPK/inhibitor crystals: A crystal of HPPK and BSS10113 consisting of a crystal space group C2 with unit cell dimensions of a=79.98, b=52.77, and c=36.69; A crystal of HPPK and BSS10124 consisting of a crystal space group P2$_1$2$_1$2 with unit cell dimensions of a=52.91, b=70.98, and c=36.38; and a crystal of HPPK and BSS 10128 consisting of a crystal space group P2$_1$2$_1$2 with unit cell dimensions of a=53.00, b=70.64, and c=36.25. The disclosure also includes a composition of matter comprising a crystal structure of HPPK with an HPPK ligand disposed therein. In certain instances the HPPK ligand contains a pterin moiety and/or is a compound of Formula I.

The disclosure includes a method for a identifying a molecule that binds to HPPK, the method comprising the steps of (a) providing a molecular target selected from the BSS10113, BSS10124, or BSS10128 binding site of HPPK, (b) using the molecular target to identify a candidate molecule that can bind to one or more said molecular targets; and (c) producing the candidate molecule identified in step (b). The molecular target selected from the BSS10113, BSS10124, or BSS10128 binding site of HPPK is obtained from the atomic coordinates of the HPPK-BSS10113, HPPK-BSS10124, or HPPK-BSS10128 supplied in Appendices 1, 2, and 3 or is a molecular model derived from the atomic coordinates supplied in these Appendices. The method may include the additional step of repeating steps (a) through (c) to identify and produce a modified candidate molecule having high binding affinity for HPPK or high potency relative to the candidate molecule.

Lead Compounds for Novel Anti-Bacterial Agents

Among the three compounds presented here, BSS10113 and BSS10128 are stable. BSS10124 is not stable, but is obviously stabilized in the HPPK•BSS10124 complex. Hence, BSS10113 and BSS10128 are the lead compounds for novel anti-bacterial agents targeting HPPK.

Figure 4:
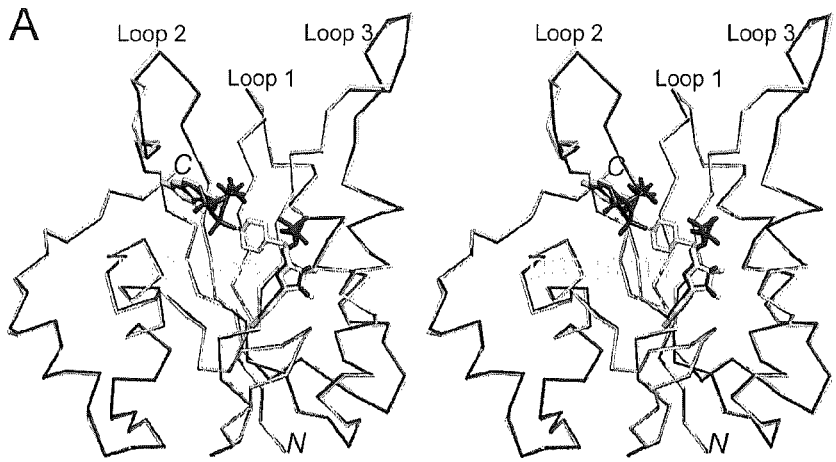
FIG. 4. Stereoview showing the superposition of (A) the HPPK•BSS10113 (disclosed here) and HPPK•AMP•HPPP (Protein Data Bank (PDB) entry 1RAO) structures and (B) the HPPK•BSS10128 (disclosed here) and HPPK•MgAMPCPP•HP (PDB entry 1Q0N) structures. Proteins are shown as Ca traces and ligands as stick models.
Figure 4:
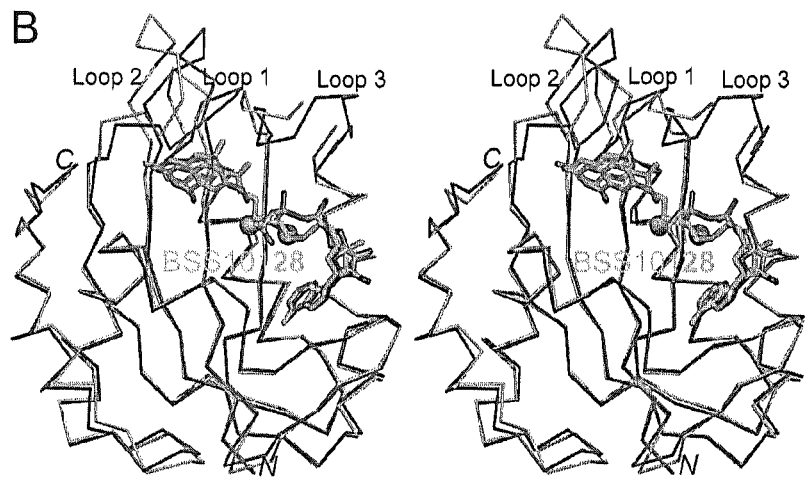

The catalytic trajectory of HPPK can be described by five consecutive states: apo-HPPK, HPPK•MgATP, HPPK•MgATP•HP, HPPK•AMP•HPPP, and HPPK•HPPP (Blaszczyk et al., Structure (2004) 12: 467-475). Among the five states, the protein in HPPK•MgATP and HPPK•AMP•HPPP exhibits the same conformation, which is also observed in the HPPK•BSS10113 complex (FIG. 4A). The protein in the HPPK•BSS10128 complex displays the conformation observed in the HPPK•MgATP•HP complex (FIG. 4B). Both complexes show stable conformations of HPPK, suggesting that the structure-based design is accurate.

Also provided herein is a method for identifying a molecule that inhibits HPPK, the method comprising: (a) providing a molecular model comprising one or more HPPK target regions (protein-inhibitor interaction sites) selected from (i) the BSS10113 binding site, (ii) the BSS10124 binding site, and (iii) the BSS10128 binding site (1) from the atomic coordinates for HPPK in complex with BSS10113, BSS10124, or BSS10128; and (b) using the molecular model to identify a candidate molecule that can bind to the molecular model. The atomic coordinated of HPPK in complex with BSS10113, BSS10124, or BSS10128 are provided with this application as Appendices 1, 2, and 3, respectively. In certain embodiments this method further comprises producing the candidate molecule identified in step (b) and can also include determining whether the produced candidate molecule inhibits HPPK.

The protein-inhibitor interaction sites can be derived with Accelrys' Discovery Studio suite, e.g., *Discovery Studio*, version 2.1; Accelrys: San Diego, Calif., 2008. Fragment searching, by which a candidate molecule may be identified can be conducted, for example, within the interaction site boxes using the De Novo Evolution and De Novo Link protocols (Accelrys) and the ZINC databases, Irwin and Shoichet, *J. Chem. Inf. Model.* (2005) 45(1):177-82.

EXAMPLES

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, may also be used in the synthetic schemes and examples.

AMPCPP α,β-methyleneadenosine 5'-triphosphate
DCM Dichloromethane
DMF Dimethyl formamide
EtOH Ethanol
HP 6-hydroxymethyl-7,8-dihydropterin
HPPK 6-hydroxymethyl-7,8-dihydropterin pyrophosphokinase
MR molecular replacement
NBS N-bromosuccinamide
PDB Protein Data Bank
TFA trifluoroacetic acid
T-HYDRO t-butyl hydroperoxide General Experimental Information The compound 2',3'-isopropylideneadenosine (1, Scheme 1) was purchased from TCI America. All other chemicals were purchased from Sigma-Aldrich. Starting materials and solvents were used without further purification. Anhydrous reactions were conducted under a positive pressure of dry $N_2$. Reactions were monitored by thin layer chromatography (TLC) on Baker-flex Silica Gel IB-F (J. T. Baker). Final compounds and intermediates were purified by flash chromatography performed on Teledyne ISCO Combiflash Rf system using RediSep Rf columns. Ion exchange chromatography was performed using strata Scx (50 μm particle size, 70 Å pore) resin cartridges. Preparative high pressure liquid chromatography (HPLC) was conducted using a Waters 600E system using a Waters 2487 dual λ absorbance detector and Phenomenex $C_{18}$ columns (250 mm×21.2 mm, 5 μm particle size, 110 Å pore) at a flow rate of 10 mL/min. A binary solvent systems consisting of A=0.1% aqueous TFA and B=0.1% TFA in acetonitrile was employed with the gradients as indicated. $^1$H and $^{13}$C NMR data were obtained on a Varian 400 MHz spectrometer and are reported in ppm relative to TMS and referenced to the solvent in which the spectra were collected. Mass spectra were measured with Agilent 1100 series LC/Mass Selective Detector, Agilent 1200 LC/MSD-SL system and Thermoquest Surveyor Finnigan LCQ deca. All compounds tested were at least 95% pure by LCMS and NMR.

General Scheme for Preparation of Compound 13.

Scheme 1

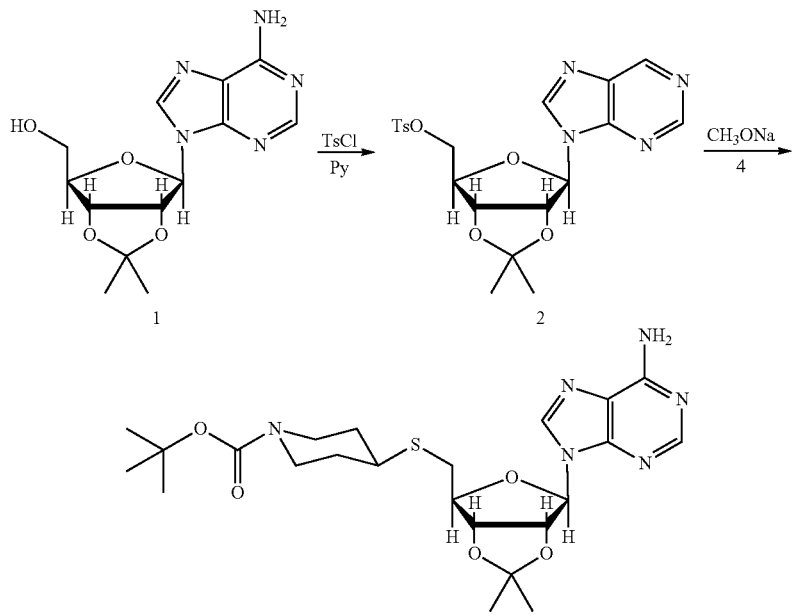

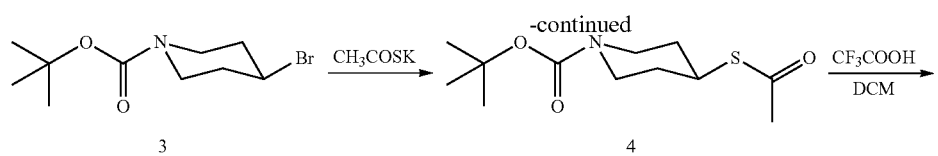
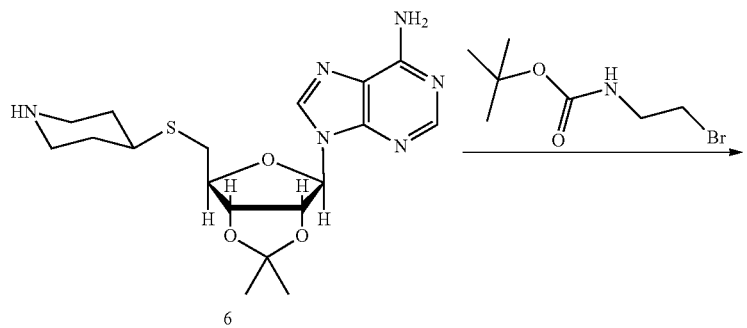
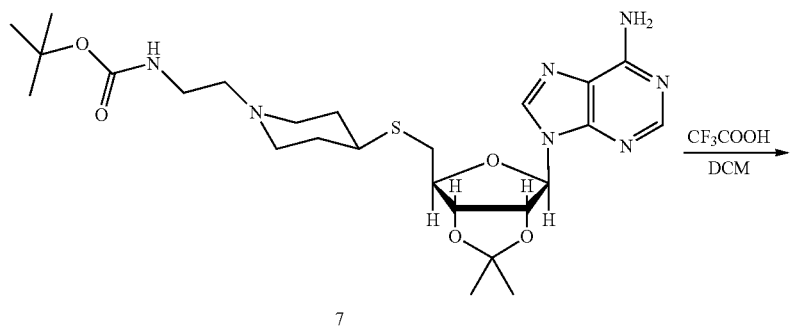
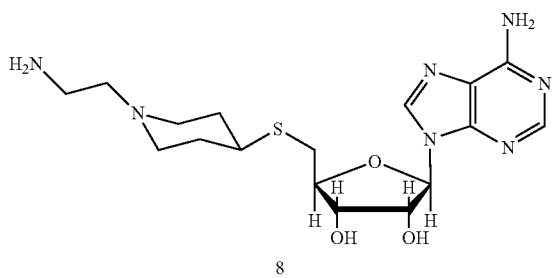
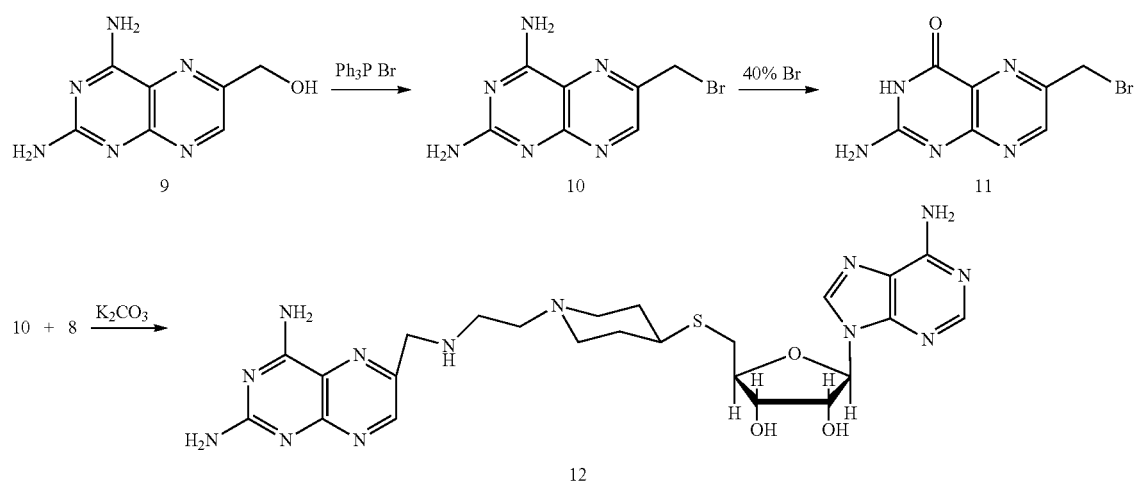

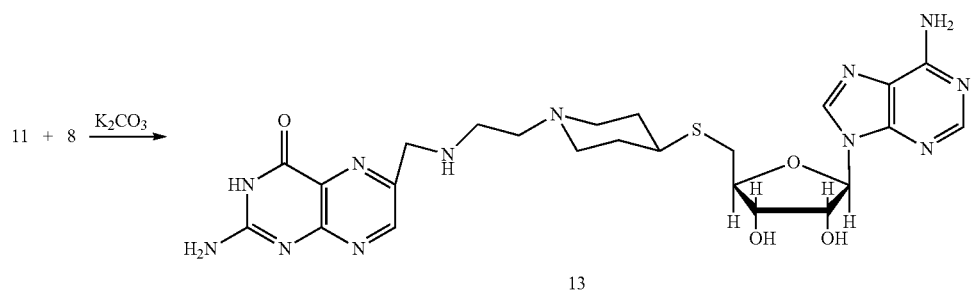
General Scheme for Preparation of Compounds 22 and 24
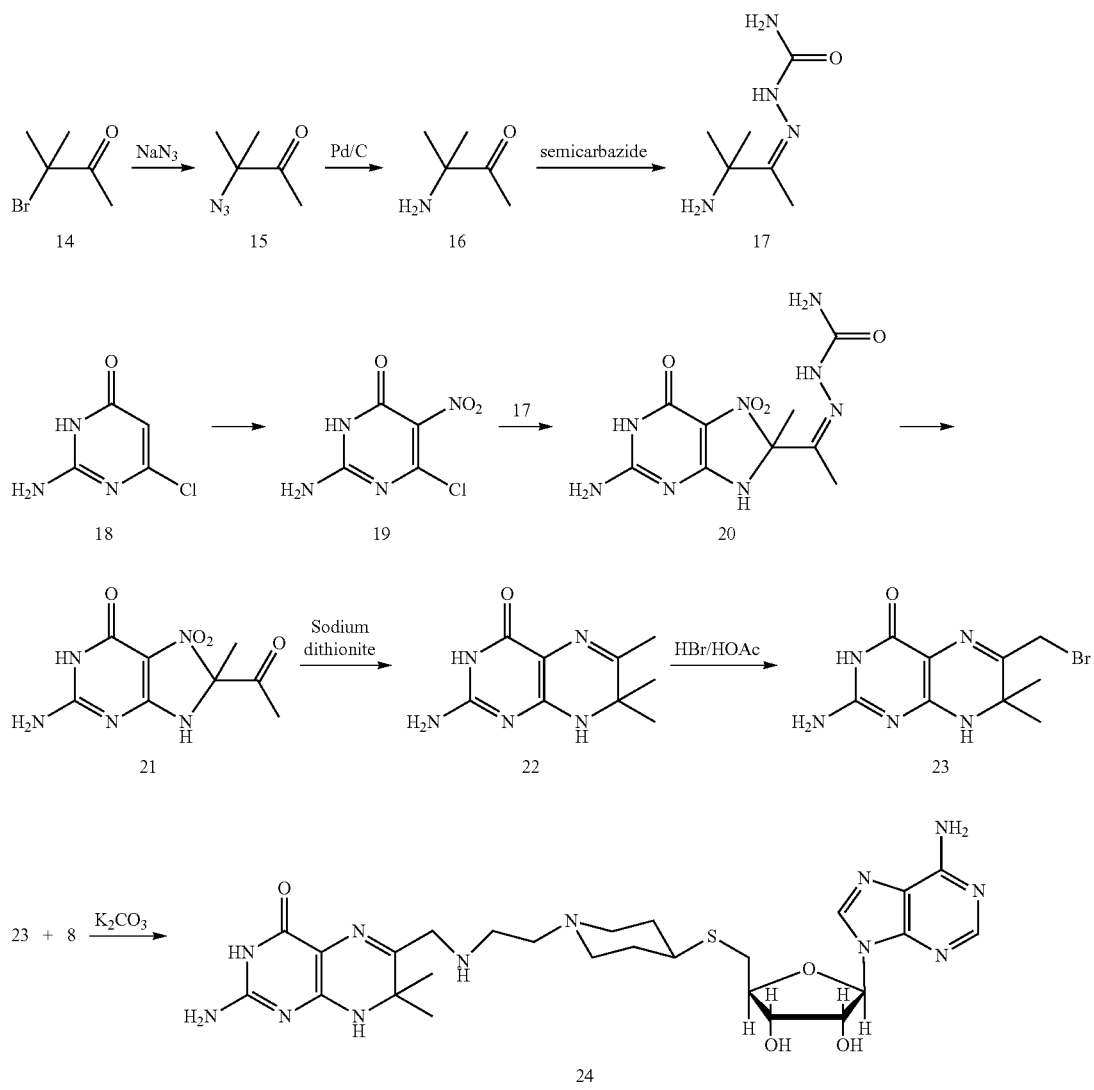

General Scheme for Preparation of Compounds 25, 26, and 28

In Scheme 1, above, isopropylideneadenosine 1 is used to synthesize toluenesulfonyl isopropylideneadenosine, 2 (2',3'-O-isopropylidene-5'-O-toluene-p-sulfonyl adenosine). An anhydrous pyridine solution of commercially available 2',3'-isopropylideneadenosine 1 is shaken with p-toluenesulfonyl chloride. In a separate reaction, the synthon 4-acetylsulfanyl-piperidine-1-carboxylic acid tert-butyl ester 4 was synthesized using the method of Plettenburg in which potassium

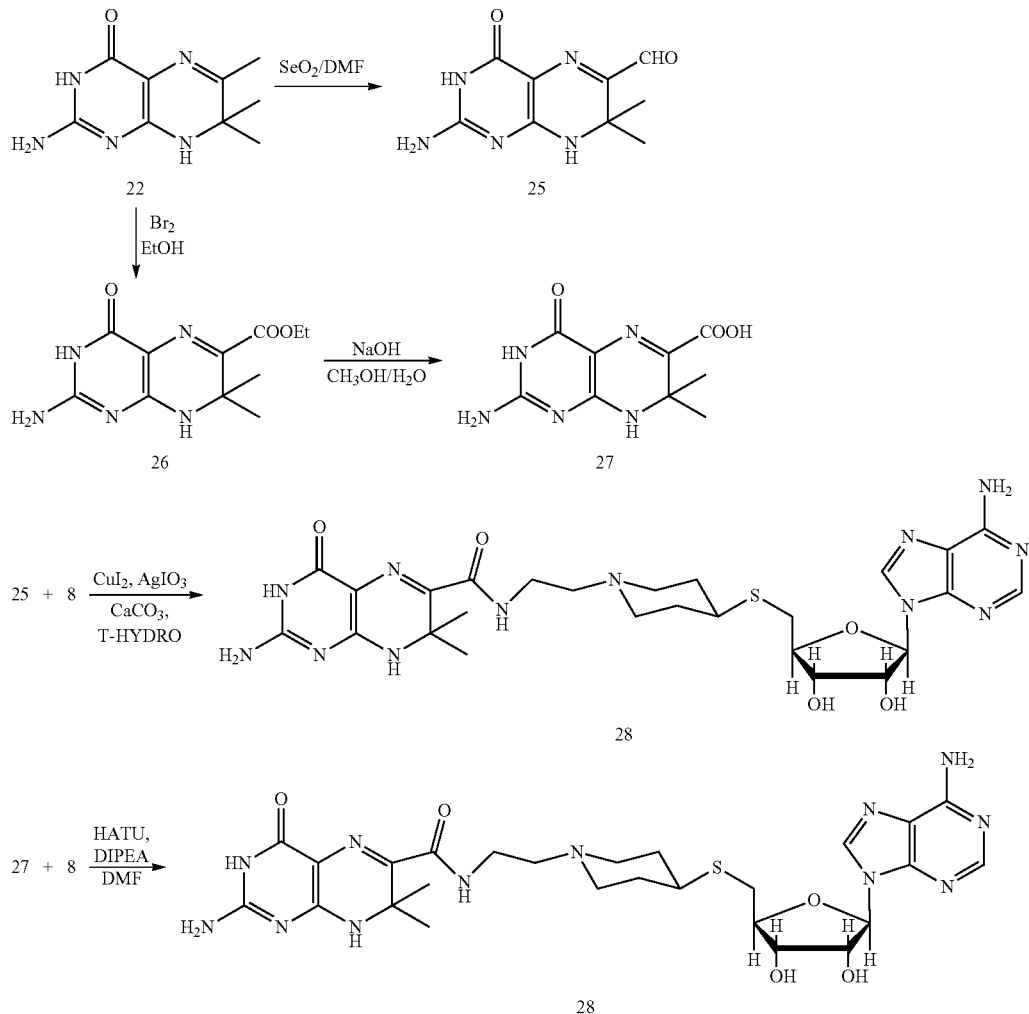

Example 1

Synthesis of 2-Amino-6-[(2-{4-[5-(6-amino-purin-9-yl)-3,4-dihydroxy-tetrahydro-furan-2-ylmethylsulfanyl]-piperidin-1-yl}-ethylamino)-methyl]-3H-pteridin-4-one (13)

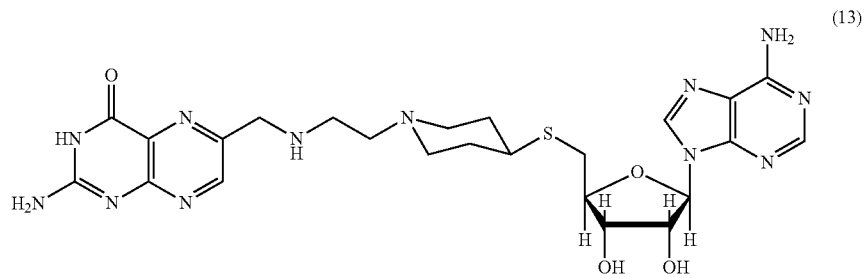

thioacetate and 4-bromo-piperidine 3 are heated in DMF. According to modified procedures based on an existing protocol (Isakovic et al., Bioorg. & Med. Chem. Lett. (2009) 19: 2742-2746), synthon 4 is reacted with sodium methoxide to form the thiol, followed by the reaction with 2 to give 4-[6-(6-Amino-purin-9-yl)-2,2-dimethyl-tetrahydro-furo[3,4-d][1,3]dioxol-4-ylmethylsulfanyl]-piperidine-1-carboxylic acid tert-butyl ester 5. Under the TFA/DCM condition, cleavage of the BOC protection group and subsequent reaction of 6 with (2-bromo-ethyl)-carbamic acid tert-butyl ester provides intermediate 7. The deprotection of 7 yields 8, which contains an amino group used to link 8 to the pterin moiety.

2,4-Diamino-6-(hydroxymethyl)pteridine hydrochloride 9 is treated with dibromotriphenylphosphorane in N,N-dimethylacetamide to give 10, which in 48% hydrobromic acid is converted through hydrolytic deamination to provide 11.

To a solution of 2-[1-(2-Amino-ethyl)-piperidin-4-ylsulfanylmethyl]-5-(6-amino-purin-9-yl)-tetrahydro-furan-3,4-diol (100.0 mg, 0.244 mmol, 1 eq) (8) and potassium carbonate (337.9 mg, 2.44 mmol, 10 eq) in 20 mL dimethylacetamide, 2-amino-6-bromomethyl-3H-pteridin-4-one (87.0 mg, 0.244 mmol, 1 eq) (11) was added and then stirred at room temperature for 24 hours. It was evaporated in high vacuum and the residue dissolved in water methanol mixture and purified by HPLC to give compound 13 (71.0 mg, 0.122 mmol, 50%) of a yellowish powder. MS (ESI) calculated for $C_{24}H_{32}N_{12}O_4S$ [M+H]+ 585.24, found 585.1

Example 2

2-Amino-7,7-dimethyl-4-oxo-3,4,7,8-tetrahydro-pteridine-6-carbaldehyde (25)

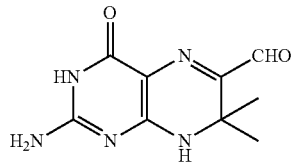 [SMILES: CC1(C)Nc2nc(N)[nH]c(=O)c2N=C1C=O]

General Description of Scheme 2

Compound 22, 2-amino-7,8-dihydro-6,7,7-trimethylpteridin-4(3H)-one, used in the synthesis of 25, 26, and 28, was synthesized by a procedure of Al-Hassan (Al-Hassan et al., (1985) 1: 1645-1659). This procedure is based on a classical method for the preparation of 7,8-dihydropteridines, the condensation of α-aminoketone with halopyrimidinone followed by reductive stylization. Accordingly, 22 was prepared by the condensation of 2-amino-5-nitro-6-chloropyrimidin-4-one (19) with 3-amino-3-methylbutan-2-one semicarbazone (17) under basic conditions. Compound 22 can be converted to 23 by Stuart's method (U.S. Pat. No. 4,036,961, which is hereby incorporated by references for its teaching regarding pteridine synthesis) using bromine in acetic acid solution (Scheme 2), or oxidized by $SeO_2$ in DMF to give 25 (Scheme 3).

Synthesis of Compound 25

Compound 25 (Scheme 3) is an intermediate useful in the preparation of compounds of Formula I. To synthesis 25, a solution of 22 (207 mg, 1.0 mmol) in DMF (10 mL) and pyridine (105 uL, 1.30 mmol) was treated with $SeO_2$ (145 mg, 1.30 mmol) and stirred at room temperature for 5 h. The reaction was then heated to 80° C. for 15 min. The solvent was evaporated under high vacuum and the residue purified by flash chromatography (silica gel, methanol:dichloromerhane=2:8) to give 25 (199 mg, 0.9 mmol, 90%) as a yellowish powder. MS (ESI) calculated for C9H11N5O2 [M+H]+ 222.09, found 222.1.

Example 3

Synthesis of 6-Carboxylic Ethyl Ester-7,7-dimethyl-7,8-dihydropterin (26)

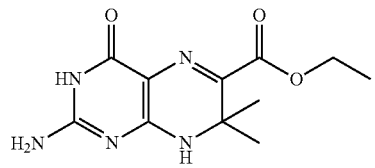

Compound 26 is an intermediate useful in the preparation of compounds of Formula I. To synthesize 26, compound 22 (0.5 g, 2.4 mmol) is dissolved in 80 mL ethanol in a heavy wall pressure vessel. Bromine (0.43 mol, 8.4 mmol) is dropped into the solution. The pressure vessel is sealed with Teflon bushing. The solution is heated overnight at 120° C. The ethanol is evaporated and the residue purified by column chromatography. The desired compound, 26, is obtained as a yellow solid (35% yield).

N-Bromosuccinimide (NBS) may be used in the above procedure in place of bromine, as the bromination agent.

In an alternate procedure compound 22 (0.5 g, 2.4 mmol) and NBS (1.28 g, 7.2 mmol) are dissolved in 20 mL ethanol. The reaction mixture is heated in a Biotage microwave initiator for 5-25 minutes. The ethanol is evaporated and the residue purified by column chromatography. Compound 26 is obtained as a yellow solid (52% yield).

Example 4

2-Amino-7,7-dimethyl-4-oxo-3,4,7,8-tetrahydro-pteridine-6-carboxylic acid (2-{4-[5-(6-amino-purin-9-yl)-3,4-dihydroxy-tetrahydro-furan-2-ylmethylsulfanyl]-piperidin-1-yl}-ethyl)-amide (28)

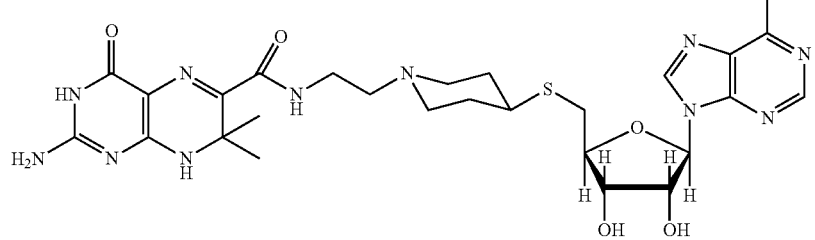

Compound 28 was synthesized by 25 and 8 using the procedure developed by Yoo and Li (J. Am. Chem. Soc. (2006) 128: 13064-13065) using copper-silver catalysis and aqueous tert-butyl hydroperoxide (Method A) or by 26 and 8 using the disclosed procedure herein with a significantly improved yield (Method B).

Synthesis of Compound 28 (Method A)

Compound 8 (12.3 mg, 0.03 mmol, 1.5 eq) was mixed with CuI (0.0388 mg, 0.0002 mmol, 1.0 mol %), AgIO$_3$ (0.057 mg, 0.0002 mmol, 1.0 mol %) and CaCO$_3$ (2.2 mg, 0.022 mmol, 1.1 eq) in DMF (0.2 mL). Compound 25 (4.5 mg, 0.020 mmol, 1.0 eq) and T-HYDRO® (70 wt % in H$_2$O, 0.00315 mL, 0.022 mmol, 1.1 eq) was added under an inert atmosphere (N$_2$) at room temperature. The reaction was allowed to stir for overnight at 40° C. The crude reaction was purified by HPLC (H$_2$O:methanol=2:3) to provide 28 (3.77 mg, 0.006 mmol, 30%) as a pale yellow solid. MS (ESI) calculated for C$_{26}$H$_{36}$N$_{12}$O$_5$S [M+H]+ 629.27, found 629.1.

Synthesis of Compound 28 (Method B)

To a solution of compound 26 (265 mg, 1 mmol, 1 eq) methanol (5 mL) was added a solution of sodium hydroxide (2M, 2 mmol, 2 eq). After stirring for two hours, the reaction mixture was acidified to pH=2 with 1M HCl, the product was precipitated, the precipitate washed once with water and then dried to obtain 2-Amino-7,7-dimethyl-4-oxo-3,4,7,8-tetrahydro-pteridine-6-carboxylic acid (27) (213 mg, 0.9 mmol, 90%). MS (ESI) calculated for C$_9$H$_{11}$N$_5$O$_3$ [M+H]+238.09, found 238.1

To a solution of compound 27 (190 mg, 0.8 mmol, 1 eq), O-(7-azabenzotriazol-1-yl)-1,1,3,3-tetramethyluronium hexafluorophosphate (HATU) (334.6, 0.88 mmol, 1.1 eq), and compound 8 (327.2 mg, 0.8 mmol, 1 eq) in anhydrous DMF (100 mL) was added DIPEA (4.18 uL, 2.4 mmol, 3q). After 18 h, the solvent was evaporated under high vacuum, the reaction residue was purified by HPLC(H2O:Methanol=2:3) to provide 28 (377 mg, 0.6 mmol, 75%) as a pale yellow solid. MS (ESI) calculated for C26H36N12O5S [M+H]+ 629.27, found 629.1.

Example 5

Data Acquisition, Structure Solution, and Refinement

X-ray diffraction data were collected at 100K with an MARCCD detector mounted at the synchrotron Beamline 22 of the Southeast Regional Collaborative Access Team (SER-CAT) at the Advanced Photon Source, Argonne National Laboratory. Data processing was carried out with the HKL2000 program suite (Otwinowski, Z. and Minor, W., Methods in Enzymology, (1997) 276: 307-326). The details of data collection and processing, and structure solution and refinement are summarized in Table 2. The structures were solved and refined with PHENIX (Adams, P. D., Acta Crystallogr. D. (2002) 58: 1948-1954). For Fourier synthesis, multiple conformations of amino acid residues, ligands, and solvent molecules were removed from the starting models. All graphics effort, including model building and rebuilding, was carried out with COOT (Emsley, P. and Cowtan, K. (2004) Acta Crystallogr. D. 60: 2126-2132). The structures were verified with annealed omit maps and the geometry of finalized structures was assessed using PROCHECK (Laskowski, R. A. et al., (1993) J. Appl. Crystallogr. 26: 283-291) and WHAT IF (Vriend, G. (1990) J. Mol. Graph. 8: 42-56, 29). Illustrations were prepared with PyMOL (DeLano Scientific LLC.).

Example 6

Biochemical Studies

Binding studies were carried out at room temperature. Protein (HPPK) and ligand stock solutions were made in 100 mM Tris-HCl, pH 8.3, and their concentrations were determined spectrophotometrically using the following extinction coefficients: 21600 M$^{-1}$ cm$^{-1}$ at 280 nm for HPPK, 7000 M$^{-1}$ cm$^{-1}$ at 366 nm for the pteridone bisubstrate inhibitors such as compound 13, and 7124 M$^{-1}$ cm$^{-1}$ at 380 nm for the tetrahydropteridine bisubstrate inhibitors such as 28. A 3-mL dilute inhibitor solution in a fluorometric cuvette was titrated with the protein stock solution. Fluorescence was measured on a Horiba Jobin Yvon FluoroMax-4 fluorometer. The excitation wavelength and slit were 364-380 and 2-3 nm, respectively, and the emission wavelength and slit were 450-482 and 2-5 nm, respectively. A few HPPK preparations showed some fluorescence at the excitation and emission wavelengths. For these HPPK preparations, a control experiment, in which a 3-mL buffer solution was titrated with the protein solution, was performed. The control data was subtracted from the titration data. The corrected titration data was then analyzed by nonlinear least-squares regression using the software Origin and the equation:

$$F_{obs} = \varepsilon_f L_t + \frac{(\varepsilon_b - \varepsilon_f)\left(L_t + E_t + K_d - \sqrt{(L_t + E_t + K_d)^2 - 4E_t L_t}\right)}{2}$$

where $F_{obs}$ is the observed fluorescence, $\varepsilon_f$ and $\varepsilon_b$ are the fluorescence coefficients of the ligand in the free and protein-bound states, respectively, $L_t$ is the total concentration of the ligand, and $E_t$ is the total concentration of HPPK. $L_t$ and $E_t$ were varied during the titration process according to the following expressions:

$$L_t = \frac{L_0 V_0}{V_0 + \Delta V}$$

and $$E_t = \frac{E_0 \Delta V}{V_0 + \Delta V}$$

where $E_0$ is the concentration of the HPPK stock solution, $L_0$ is the initial concentration of the ligand, $V_0$ is the initial volume of the titration, and $\Delta V$ is the total volume of the added HPPK solution.

Figure 2:
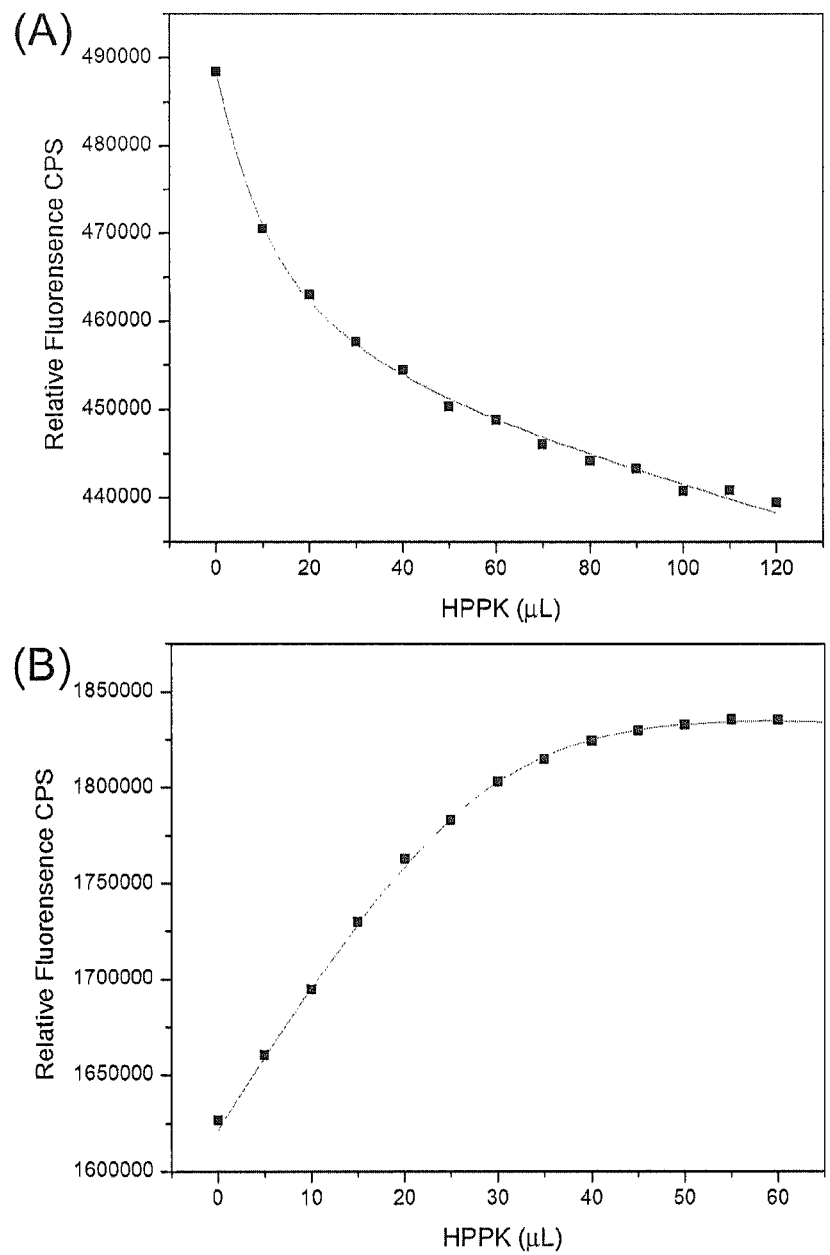
FIG. 2. The titration curve of (A) BSS10113 and (B) BSS10128 for binding studies.

The titration curves for 13 and 28 of binding analysis is shown in FIG. 2. The $K_d$ value was obtained by nonlinear least-squares analysis. It was 0.59 (0.19) µM for 13 and 0.33 (0.05) µM for 28. Compound 24 was not as stable as 13 and 28, and therefore, its $K_d$ was not determined.

While specific embodiments have been shown and described, various modifications and substitutions can be made thereto without departing from the spirit and scope of the invention. Accordingly, it is to be understood that the present invention has been described by way of illustration and not limitations.

We claim:

1. A compound or pharmaceutically acceptable salt thereof of the formula:

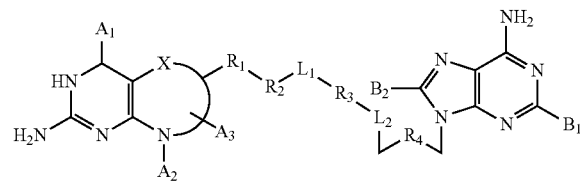

wherein:

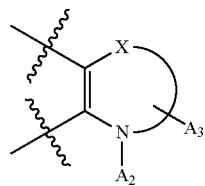

is a 5 or 6-membered heterocyclic ring;

X is nitrogen, —N($A_5$)-, —C($A_6$)-, or —C($A_6A_7$)-;

$A_1$ is hydrogen, oxo, amino, or amino$C_1$-$C_2$alkyl;

$A_2$ is absent, hydrogen, or $C_1$-$C_2$alkyl;

$A_3$ is absent, or one or two substituents independently chosen from hydrogen, halogen, $C_1$-$C_2$alkyl, and $C_1$-$C_2$alkoxy;

$A_5$ is hydrogen or $C_1$-$C_4$alkyl;

$A_6$ and $A_7$ are independently hydrogen, $C_1$-$C_4$alkyl, or $C_1$-$C_4$alkoxy;

$R_1$ is methylene optionally substituted with hydroxyl, halogen, $C_1$-$C_2$alkyl, or oxo;

$R_2$ is chosen from —NH—, —SH—, —S(=O)—, —S(=O)$_2$—, —P(=O)—, and —P(=O)$_2$—;

$L_1$ is an alkylene linker having from 1 to 4 carbon atoms, optionally containing 1 heteroatom selected from oxygen, nitrogen, and sulfur, and optionally containing 1 to 2 carbon-carbon double bonds, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy;

$R_3$ is absent or $R_3$ is an amide, heteroalkylene, cycloalkyl, heterocycloalkyl, phenyl, or 5- or 6-membered heteroaryl; and $R_3$ is unsubstituted or substituted with 1 or more substituents independently chosen from hydroxyl, halogen, amino, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy;

$L_2$ is absent or $L_2$ is an alkylene linker having from 1 to 4 carbon atoms, optionally containing 1 heteroatom selected from oxygen, nitrogen, sulfur, and phosphorus and optionally containing 1 to 2 carbon-carbon double bonds, wherein $L_2$ is unsubstituted or substituted with 1 or more substituents independently chosen from oxo, hydroxyl, halogen, amino, $C_1$-$C_4$alkyl, $C_1$-$C_4$alkoxy, $C_1$-$C_2$haloalkyl, and $C_1$-$C_2$haloalkoxy;

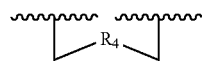

is a 5- or 6-membered monosaccharide ring or is an alkylene or heteroalkylene linker having from 1 to 4 chain atoms; and $B_1$ and $B_2$ are independently chosen from hydrogen, halogen, hydroxyl, amino, $C_1$-$C_2$alkyl, $C_1$-$C_2$alkoxy, mono- or di-$C_1$-$C_2$alkylamino, amino$C_1$-$C_2$alkyl, $C_1$-$C_2$haloalkyl, and $C_1$-$C_2$haloalkoxy.

2. A compound or salt of claim 1 of the formula

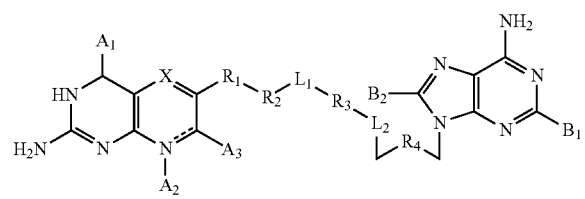

wherein $A_2$ is absent or hydrogen;

$A_3$ is one or two substituents independently chosen from hydrogen, halogen, $C_1$-$C_2$alkyl, and $C_1$-$C_2$alkoxy; and X is N or —C($A_6$)-.

3. A compound or salt thereof of claim 2, having the formula:

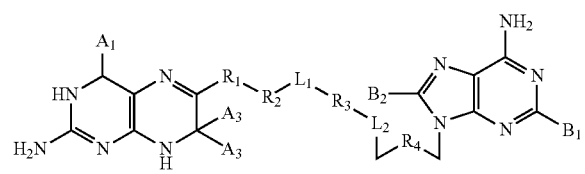

wherein:

$A_3$ are each independently hydrogen, halogen, methyl, or methoxy;

$R_3$ is a 5- or 6-membered heterocycloalkyl group having 1 or 2 nitrogen ring atoms with remaining ring atoms being carbon, and $R_3$ is unsubstituted or substituted with 1 or more substituents independently chosen from hydroxyl, halogen, amino, and $C_1$-$C_2$alkyl, $C_1$-$C_2$alkoxy; and

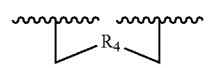

is a 5- or 6-membered monosaccharide ring.

4. A compound or salt thereof of claim 2, having the formula:

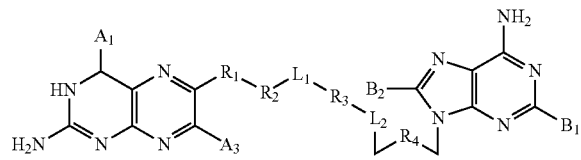

wherein:

$A_3$ is hydrogen, halogen, methyl, or methoxy;

$R_3$ is a 5- or 6-membered heterocycloalkyl group having 1 or 2 nitrogen ring atoms with remaining ring atoms being carbon, and $R_3$ is unsubstituted or substituted with 1 or more substituents independently chosen from hydroxyl, halogen, amino, and $C_1$-$C_2$alkyl, $C_1$-$C_2$alkoxy; and

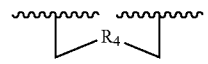

is a 5 or 6-membered monosaccharide ring.

5. A compound or salt thereof of claim 2, wherein $A_1$ is oxo and each $A_3$ is independently chosen from hydrogen and methyl; and $R_2$ is —NH—.

6. A compound or salt thereof of any one of claim 5, wherein $R_1$ is methylene optionally substituted with —(C=O)—.

7. A compound or salt thereof of claim 2, wherein $L_1$ is an alkylene linker having from 2 to 4 carbon atoms, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy; and $L_2$ is an alkylene linker having from 1 to 2 carbon atoms, containing 1 heteroatom selected from oxygen, nitrogen, and sulfur, wherein $L_2$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy; wherein the total number of carbon atoms in the $L_1$ and $L_2$ alkylene linkers is from 3 to 5.

8. A compound or salt thereof of claim 7, wherein $L_1$ is an alkylene linker having from 2 to 3 carbon atoms, wherein $L_1$ is unsubstituted or substituted with 1 or more substituents independently chosen from halogen and methyl; $L_2$ is an alkylene linker of the formula —$SCH_2$—, wherein $L_2$ is unsubstituted or substituted with 1 or more substituents independently chosen from halogen and methyl; and $R_3$ is a piperidinyl, piperazinyl, or pyrrolidinyl ring; each of which $R_3$ is unsubstituted or substituted with 1 or more substituents independently chosen from hydroxyl, halogen, $C_1$-$C_2$alkyl, and $C_1$-$C_2$alkoxy.

9. A compound or salt thereof of any one of claim 2, wherein

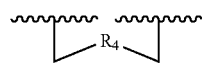

is a 5 or 6-membered monosaccharide ring selected from d-ribose, d-arabinose, d-xylose and d-lyxose.

10. A compound or salt thereof of claim 2 wherein $R_4$ is d-ribose and $B_1$ and $B_2$ are both hydrogen.

11. A compound or salt thereof of claim 1 of the formula

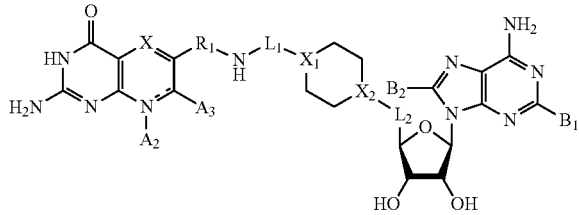

wherein:
$A_1$ is oxo;
$A_2$ is absent or hydrogen;
$A_3$ is one or two substituents independently chosen from hydrogen and $C_1$-$C_2$ alkyl;
X is N or —$C(A_6)$-;
$X_1$ and $X_2$ are independently CH or N;
$R_1$ is methylene optionally substituted with —(C=O)—;
$L_1$ is an alkylene linker having from 2 to 4 carbon atoms, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy;
$L_2$ is an alkylene linker having from 1 to 2 carbon atoms, containing 1 heteroatom selected from oxygen, nitrogen, and sulfur, wherein $L_2$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy; and
$B_1$ and $B_2$ are independently hydrogen or methyl.

12. A compound or salt thereof of claim 1, wherein the compound is:

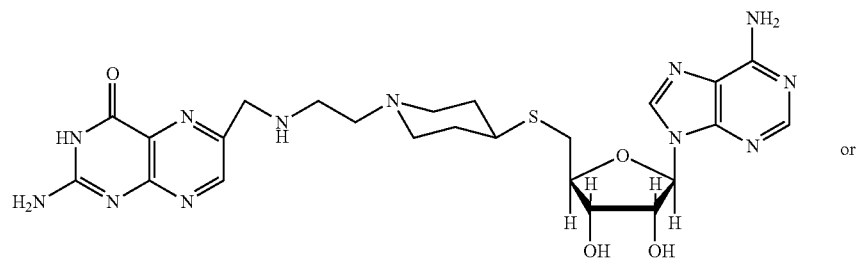

or

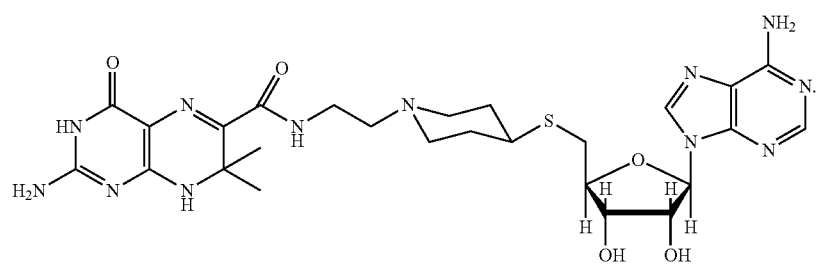

13. A pharmaceutical composition comprising a compound or salt of any claim 1 and a pharmaceutically acceptable carrier.

14. A method of treating a bacterial infection responsive to HPPK modulation, the method comprising providing a therapeutically effective amount of compound of claim 1 to a patient having a bacterial infection responsive to HPPK modulation.

\* \* \* \* \*